United States Patent [19]

Werther et al.

[11] 4,268,440
[45] May 19, 1981

[54] PREPARATION OF CAPROLACTAM

[75] Inventors: Joachim Werther, Bobenheim-Roxheim; Hugo Fuchs, Ludwigshafen; Uwe Brand, Rosengarten; Friedrich R. Faulhaber, Mutterstadt, all of Fed. Rep. of Germany

[73] Assignee: BASF Aktiengesellschaft, Fed. Rep. of Germany

[21] Appl. No.: 129,827

[22] Filed: Mar. 13, 1980

[30] Foreign Application Priority Data

Apr. 14, 1979 [DE] Fed. Rep. of Germany ....... 2915360

[51] Int. Cl.³ .......................................... C07D 201/04
[52] U.S. Cl. .............................................. 260/239.3 A
[58] Field of Search ................................. 260/239.3 A

[56] References Cited

U.S. PATENT DOCUMENTS

| 3,154,539 | 10/1964 | Irnich | 260/239.3 A |
| 3,210,338 | 10/1965 | Huber et al. | 260/239.3 A |
| 3,350,393 | 10/1967 | Petri et al. | 260/239.3 A |
| 3,586,668 | 6/1971 | Immel et al. | 260/239.3 A |
| 4,137,263 | 1/1979 | Immel et al. | 260/566 A |

FOREIGN PATENT DOCUMENTS 881276  11/1961  United Kingdom ........ 260/239.3 A

Primary Examiner—Robert T. Bond
Attorney, Agent, or Firm—Keil & Witherspoon

[57] ABSTRACT

A process for the preparation of caprolactam wherein, in a first stage, cyclohexanone-oxime is vaporized, in the presence of inert gases, by bringing it into contact with a fluidized bed of inert solid particles at from 150° to 250° C., and the mixture of cyclohexanone-oxime vapor and inert gases is passed into a second stage, where the cyclohexanone-oxime is rearranged to caprolactam at from 230° to 450° C. over a supported catalyst, containing boron trioxide, in a fluidized bed.

3 Claims, No Drawings

PREPARATION OF CAPROLACTAM

The present invention relates to a process for the preparation of caprolactam, wherein, in a first stage, cyclohexanone-oxime is vaporized, in the presence of inert gases, and the mixture of cyclohexanone-oxime vapor and inert gases is passed into a second stage, in which cyclohexanone-oxime is rearranged to caprolactam at from 230° to 450° C. over a supported catalyst, containing boron trioxide, in a fluidized bed.

German Pat. No. 1,195,318 describes a process for the catalytic rearrangement of cyclohexanone-oxime, wherein liquid cyclohexanone-oxime is passed into a fluidized bed of an acid catalyst, where it vaporizes and at the same time undergoes rearrangement. However, in this process it is not possible to avoid a certain degree of decomposition of cyclohexanone-oxime, resulting in cracked products which deposit on the catalyst and damage the latter. Furthermore, impurities which are difficult to remove lower the quality of the caprolactam obtained. In particular, such impurities result in a higher UV absorption and an increased permanganate titer. It requires considerable technical effort to obtain pure caprolactam which conforms to the requirements in respect of UV absorption and permanganate titer. It has also been disclosed, in German Pat. No. 1,195,318, first to vaporize cyclohexanone-oxime in a falling film vaporizer and then to rearrange the cyclohexanone-oxime vapor in a second stage. However, the said Patent points out that separate vaporization in a falling film vaporizer does not prove successful. Further, German Laid-Open Application DOS 2,641,414 describes a process in which cyclohexanone-oxime is vaporized in a falling film vaporizer under specific conditions of pressure and temperature. However, this process requires the circulation of substantial amounts of cyclohexanone-oxime at a high temperature. Furthermoe, it is expensive to match the rate of vaporization to the operating needs.

It is an object of the present invention to carry out the catalytic rearrangement of cyclohexanone-oxime in such a way that the decomposition of the cyclohexanone-oxime and the formation of impurities which are difficult to remove, are minimized.

We have found that this object is achieved by a process for the preparation of caprolactam, wherein, in a first stage, cyclohexanone-oxime is vaporized in the presence of inert gases, and the mixture of cyclohexanone-oxime vapor and inert gases is passed into a second stage where the cyclohexanone-oxime is rearranged to caprolactam at from 230° to 450° C. over a supported catalyst, containing boron trioxide, in a fluidized bed, the cyclohexanone-oxime being vaporized, in the first stage, by bringing it into contact with a fluidized bed of inert solid particles at from 150° to 250° C.

The novel process has the advantage that the caprolactam obtained has a lower UV extinction and permanganate titer, and hence its purification is simpler. Furthermore, it is not necessary to circulate large quantities of cyclohexanone-oxime at a high temperature, and the amount of cyclohexanone-oxime to be vaporized can easily be regulated and be suited to changes in the rearrangement stage. Finally, the novel process is less detrimental to the rearrangement catalyst.

According to the invention, cyclohexanone-oxime is vaporized, in a first stage, by bringing it into contact with a fluidized bed of inert solid particles. Examples of suitable solid particles are glass beads, aluminum oxide in its various modifications, e.g. $\gamma$-aluminum oxide or boehmite, silica, titanium dioxide or compounds of the said oxides with one another, for example aluminum silicates, as well as quartz sand; the latter has proved particularly suitable. The mean particle size of the solid particles is advantageously from 0.02 to 1.0 mm. The inert gases used are preferably nitrogen or carbon dioxide, especially the former. Advantageously, from 0.1 to 10 kg of inert gases are used per kilogram of cyclohexanone-oxime to be vaporized. Before entering the fluidized bed, the inert gases are advantageously preheated to 50°-250° C. Preferably, the residence time of the cyclohexanone-oxime during vaporization in the fluidized bed is from 0.01 to 30 seconds. Further, it has proved advantageous to utilize, in the vaporization stage, the heat liberated in the rearrangement stage. This may be achieved, for example, by removing the heat from the rearrangement stage by means of a heat transfer medium which passes through cooling coils, and then using the hot heat transfer medium to heat the solid particles in the vaporization stage. The vaporization in the fluidized bed is carried out at from 150° to 250° C., especially from 180° to 220° C. The cyclohexanone-oxime to be vaporized may be introduced into the fluidized bed either as a solid or, advantageously, as a liquid. The cyclohexanone-oxime used advantageously contains from 1 to 10, especially from 3 to 7, % by weight of water. The cyclohexanone-oxime to be vaporized is advantageously injected into the fluidized bed together with a proportion of the inert gases. According to the invention, cyclohexanone-oxime is vaporized at the rate at which it is fed to the fluidized bed.

The mixture of cyclohexanone-oxime vapor and inert gases, which leaves the fluidized bed in the first stage, and which may in addition contain small amounts of water, corresponding to the water content of the cyclohexanone-oxime used, is passed into a second stage where the cyclohexanone-oxime is rearranged to caprolactam at from 230° to 450° C., especially from 270° to 370° C., over a supported catalyst, containing boron trioxide, in a fluidized bed. The rearrangement, like the vaporization of the cyclohexanone-oxime in the first stage, may be carried out under reduced pressure, atmospheric pressure or slightly superatmospheric pressure.

The catalyst used is a conventional catalyst in which boron trioxide, or boric acid which under the reaction conditions is converted to boron trioxide, is present on a carrier. Suitable carriers are, in particular, aluminum oxide in its various modifications, such as $\gamma$-aluminum oxide or boehmite, as well as silica or titanium dioxide or mixtures of such oxides, and also compounds of the oxides with one another, for example aluminum silicates. The weight ratio of boron trioxide to carrier is in general from 1:9 to 1:1. In the preferentially used catalysts the proportion of boron trioxide is from 25 to 50% by weight. The catalysts may additionally be modified by means of additives, for example manganese, cobalt or nickel used in an amount of up to 10% by weight, based on boron trioxide and calculated as metal. These metals are added, when preparing the catalyst, in the form of salts, eg. nitrates or fatty acid salts, which on heating are converted to the corresponding oxides. Accordingly, the metals are present in the finished catalyst as oxides or as their compounds with boron trioxide. The catalysts are prepared in the conventional manner. For example, the carrier is impregnated with boric acid or an ammonium borate solution, dried at from 50° to 500°

C. and then calcined at from 600° to 1,200° C. in order to convert the applied compounds to the corresponding mixed phases with boron trioxide. The catalysts are molded in the conventional manner, for example by working the boron trioxide and carrier into a paste with a small amount of water, mixing this in a kneader, forming the composition into extrudates or pills, and drying and calcining these at the stated temperatures. Advantageously, the particle size of the finished catalyst is from 0.05 to 1.5 mm, especially from 0.2 to 1.0 mm. The height of the catalyst bed is advantageously such as to give a residence time of the cyclohexanone-oxime therein of from 0.01 to 30 seconds, especially from 0.1 to 5 seconds.

Caprolactam is advantageously isolated from the caprolactam-containing gas obtained, by chilling with caprolactam or stepwise by chilling first with caprolactam and then with water, in a column. The inert gas which is separated off is freed from water and is then advantageously recycled to the first stage, where the cyclohexanone-oxime is vaporized.

Caprolactam prepared by the process of the invention may be used for the preparation of polycaprolactam.

The Examples which follow illustrate the process according to the invention.

EXAMPLE 3 kg of a quartz sand of particle size from 0.1 to 0.5 mm are fluidized by means of 3,500 liters (S.T.P.)/h of nitrogen in a vertical electrically heated tube, having a length of 1,000 mm and a diameter of 100 mm, and provided with a perforated bottom plate. The temperature in the fluidized sand is about 250° C. 5.5 kg per hour of liquid cyclohexanone-oxime containing 4.2% of water are introduced into the fluidized bed through a nozzle with the aid of a stream of nitrogen of 1,500 l (S.T.P.)/h, and are vaporized in the bed. The resulting vapor mixture passes through a cyclone to remove dust particles and is then introduced, through a perforated bottom plate, into a second reactor having a length of 2,000 mm and diameter of 100 mm. This reactor contains 1,200 g of an aluminium oxide-boron trioxide catalyst containing 53% of aluminum oxide and 47% of boron trioxide and having a particle size of from 0.2 to 1.0 mm. This reactor is at 350° C. The fluidized bed contains a cooling coil which is connected to a second cooling coil in the fluidized sand bed of the vaporizer. Circulation of oil is maintained between the two cooling coils. The heat liberated during the rearrangement is in this way removed and re-utilized to vaporize the oxime. 2.5 kg per hour of catalyst are removed from the reactor and the same amount of fresh catalyst is introduced. The mixture of vapors leaving the reactor is passed into a column with bubble-cap trays. The lower-boiling constituents are taken off at the top of the column whilst the crude caprolactam is condensed. This crude caprolactam has a permanganate titer of 3,000 and a UV number of 4,800. The yield of caprolactam after distillation under reduced pressure is 95.1%, based on anhydrous cyclohexanone-oxime employed.

The discharged catalyst shows a loss of weight of 3.3% when heated in air at 800° C. for 5 hours.

COMPARATIVE EXAMPLE 1,200 g of the boron trioxide catalyst described in Example 1 are introduced into a vertical electrically heated tube, having a length of 2,000 mm and a diameter of 100 mm and provided with a perforated plate at its lower end, and are heated therein to 350° C. The catalyst is fluidized by blowing in 3,500 liters (S.T.P.)/h of nitrogen. 5.5 kg of cyclohexanone-oxime containing 4.2% of water are introduced through a nozzle, with the aid of a stream of nitrogen of 1,500 liters (S.T.P.)/h, and are subjected to rearrangement. The heat of rearrangement is removed via a cooling coil which is located in the fluidized bed, and is filled with oil and connected to a thermostat. At the same time, 2.5 kg per hour of catalyst are discharged from the reactor. The vapor mixture leaving the reactor is passed into a column fitted with bubble-cap trays. There, the low-boiling constituents are removed at the top of the column and the crude lactam is condensed, as described in Example 1.

The crude lactam obtained has a permanganate titer of 6,000 and a UV number of 8,500. The yield of caprolactam, after distillation under reduced pressure, is 94.0% of theory, based on anhydrous cyclohexanone-oxime employed.

The discharged catalyst shows a loss of weight of 5.5% when heated in air at 800° C. for 5 hours.

We claim:

1. A two-stage process for the preparation of caprolactam which comprises:
   (a) heating cyclohexanone-oxime, in the presence of inert gases, in contact with a fluidized bed of inert solid particles at a temperature of from 180° to 220° C., in a first-stage to vaporize cyclohexanone-oxime;
   (b) passing the vaporized cyclohexanone-oxime mixed with the inert gases to a second-stage, and
   (c) heating the mixture of vaporized cyclohexanone-oxime and inert gases in contact with a fluidized bed of catalyst containing boron trioxide, to a temperature of from 230° to 450° C., to form caprolactam by re-arrangement in said second-stage.

2. A two-stage process for the preparation of caprolactam as recited in claim 1, wherein said inert gases are in the proportion of from 0.1 to 10 kg of inert gases to each kilogram of cyclohexanone-oxime to be vaporized.

3. A two-stage process for the preparation of caprolactam as recited in claim 1, which also comprises:
   (a) recovering the heat released in the re-arrangement of cyclohexanone-oxime in the second-stage, and
   (b) heating the cyclohexanone-oxime, the inert gases and the fluidized bed of inert solid particles in the first-stage with this heat recovered from the second-stage.

* * * * *